(12) United States Patent
Li et al.

(10) Patent No.: US 11,819,822 B2
(45) Date of Patent: Nov. 21, 2023

(54) SILICA COMPOSITE MONOLITH AS A SOLID PHASE EXTRACTION MATERIAL

(71) Applicant: THE GOVERNORS OF THE UNIVERSITY OF ALBERTA, Edmonton (CA)

(72) Inventors: Xing-Fang Li, Edmonton (CA); Zhongshan Liu, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 335 days.

(21) Appl. No.: 16/778,876

(22) Filed: Jan. 31, 2020

(65) Prior Publication Data
US 2020/0246778 A1  Aug. 6, 2020

Related U.S. Application Data

(60) Provisional application No. 62/799,263, filed on Jan. 31, 2019.

(51) Int. Cl.
| | | |
|---|---|---|
| *B01J 20/24* | (2006.01) | |
| *B01J 20/283* | (2006.01) | |
| *C07C 29/76* | (2006.01) | |
| *G01N 1/40* | (2006.01) | |
| *G01N 1/22* | (2006.01) | |
| *G01N 1/10* | (2006.01) | |
| *B01J 20/10* | (2006.01) | |
| *B01J 20/26* | (2006.01) | |
| *B01J 20/285* | (2006.01) | |

(Continued)

(52) U.S. Cl.
CPC .............. *B01J 20/24* (2013.01); *B01D 15/08* (2013.01); *B01J 20/103* (2013.01); *B01J 20/262* (2013.01); *B01J 20/283* (2013.01); *B01J 20/285* (2013.01); *B01J 20/288* (2013.01); *B01J 20/28045* (2013.01); *C07C 29/76* (2013.01); *C07K 1/16* (2013.01); *G01N 1/10* (2013.01); *G01N 1/2214* (2013.01); *G01N 1/405* (2013.01); *B01J 2220/46* (2013.01); *B01J 2220/54* (2013.01)

(58) Field of Classification Search
CPC . B01J 20/283; B01J 20/103; G01N 2030/528; G01N 30/48; G01N 30/482; G01N 30/484; G01N 1/405; B01D 15/08; C07C 29/74; C07C 29/76; C07K 1/16; C07K 1/165; C07K 1/18; C07K 1/20; C07K 1/22
See application file for complete search history.

(56) References Cited

U.S. PATENT DOCUMENTS 5,086,085 A * 2/1992 Pekala .................. C08G 12/32
521/181
7,947,174 B2 * 5/2011 Malik .............. G01N 27/44721
210/656

FOREIGN PATENT DOCUMENTS

WO  WO-2005079975 A1 * 9/2005 ............ B01J 20/288

OTHER PUBLICATIONS

Pham et al. (Appl. Mater. Interfaces, 2014, 6, 14181-14188) "Superhydrophobic Silanized Melamine Sponges as High Efficiency Oil Absorbent Materials" (Year: 2014).*

(Continued)

*Primary Examiner* — Ryan B Huang
(74) *Attorney, Agent, or Firm* — Bennett Jones LLP

(57) ABSTRACT

A silica monolith nested in a polymer sponge may be formed by applying a hydrolyzed mixture of siloxanes to a melamine-formaldehyde sponge, and may be used in methods of solid phase extraction.

13 Claims, 11 Drawing Sheets

(51) Int. Cl.
*B01J 20/288* (2006.01)
*B01J 20/28* (2006.01)
*B01D 15/08* (2006.01)
*C07K 1/16* (2006.01)

(56) References Cited

OTHER PUBLICATIONS

T. Nema, E.C. Chan, & P.C. Ho, Extraction of ketamine from urine using a miniature silica monolithic cartridge followed by quantification with liquid chromatography tandem mass spectrometry (LC-MS/MS), Journal of Separation Science, 2011, 1041-1046, vol. 34, Department of Pharmacy, National University of Singapore, Singapore.

M. Dong et al., Coupling Strong Anion-Exchange Monolithic Capillary with MALDI-TOF MS for Sensitive Detection of Phosphopeptides in Protein Digest, Analytical Chemistry, 2010, 2907-2915, vol. 82, Nanjing University, Nanjing, China.

Z. Zhang et al., Preparation of Perphenylcarbomoylated β-Cyclodextrin-silica Hybrid Monolithic Column with "One-Pot" Approach for Enantioseparation by Capillary Liquid Chromatography, Analytical Chemistry, 2011, 3616-3622, vol. 83, Dalian Institute of Chemical Physics, Dalian, China.

J. Liu et al., Monolithic Capillary Column Based Glycoproteomic Reactor for High-Sensitive Analysis of N-Glycoproteome, Analytical Chemistry, 2013, 2847-2852, vol. 85, Dalian Institute of Chemical Physics, Dalian, China.

S. Miyazaki et al., Development of a monolithic silica extraction tip for the analysis of proteins, Journal of Chromatography A, 2004, 19-25, vol. 1043, GL Sciences Inc., Saitama, Japan.

G. Hayase et al., Polymethylsilsesquioxane-Cellulose Nanofiber Biocomposite Aerogels with High Thermal Insulation, Bendability, and Superhydrophobicity, American Chemical Society Applied Materials & Interfaces, 2014, 9466-9471, vol. 6, Kyoto University, Kyoto, Japan.

* cited by examiner

SILICA COMPOSITE MONOLITH AS A SOLID PHASE EXTRACTION MATERIAL

FIELD OF THE INVENTION

The present invention relates to a composite silica monolith nested in sponge (SiMNS), and the use of silica monolith in environmental studies.

BACKGROUND

Solid phase extraction (SPE) is one of the most widely used techniques for sample preparation because of its capabilities to concentrate analytes at trace/ultra-trace levels for quantification and to remove matrix interference. A desirable SPE cartridge should provide efficient retention, selectivity, and a high capacity for target analytes. Existing SPE cartridges are mostly prepared by packing particle sorbents. Particle sizes of 30-105 µm are usually utilized to balance the diffusional mass-transfer of analytes and the back pressure of cartridges. However, large-size particles often create non-uniform packing and inter-particle voids that are detrimental to extraction performance.

Silica monoliths as a chromatographic stationary phase has gained popularity in micro-scale liquid chromatographic separations over the past two decades. Compared to particle-based materials, silica monoliths possess the features of uniform through-pore and large surface area; and thus capillary monolithic columns enable rapid and efficient separation at relative low back pressure. Importantly, silica monoliths can be tuned with various surface properties, such as reversed-phase, hydrophilic interaction, ion exchange boronate affinity, chiral and molecular imprinting recognition sites. In addition to their application in chromatographic separations, silica monoliths have been fabricated in narrow capillaries, tips, and small syringe SPE cartridges for selective extractions of biological samples. However, the application of silica monolith SPE cartridges for environmental analysis is scarce. The main reason is that analysis of environmental samples, such as water, generally requires large-size SPE cartridges/columns for processing large volume of water samples. However, the preparation of large size silica monolith SPE cartridges is extremely difficult due to the shrinkage and brittleness of the silica monolith. For instance, to obtain a silica monolith with suitable diameter for packing inside the cartridge, Nema et al. had to optimize a mould size by repetitive experiments. Due to the shrinkage of the silica monolith, the mould had to be slightly bigger than the internal diameter of the empty cartridge. The preparation conditions require stringent control and are difficult to repeat.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

In one aspect, embodiments of the invention may provide monolithic materials that maintain the merits of silica monoliths and overcome the problems in producing large-size monolithic SPE cartridges for environmental analyses. Nested monolith-sponge materials may have tunable surfaces and mechanical flexibility necessary for the production of various sizes of SPE cartridges for environmental analyses.

In one aspect, the invention comprises a method of synthesizing a nested monolith-sponge material using melamine-formaldehyde (MF) sponge as a skeleton to stabilize the silica monolith sorbents, yielding a new type of silica monolith nested in sponge (SiMNS). The MF sponge offers high porosity, while the flexible framework keeps its shape and stability. In some embodiments, the MF sponge may be further modified with a hydrolyzed mixture of tetramethoxysilane (TMOS) and vinyltrimethoxysilane (VTMS). Gel formation within the sponge pores results in the generation of the new SiMNS material.

Aspects of the invention relate to synthesis of SiMNS, surface-functionalization of SiMNS, construction of SPE cartridges with the functionalized SiMNS materials, and an application of water analysis.

BRIEF DESCRIPTION OF THE DRAWINGS

In the drawings shown in the specification, like elements may be assigned like reference numerals. The drawings are not necessarily to scale, with the emphasis instead placed upon the principles of the present invention. Additionally, each of the embodiments depicted are but one of a number of possible arrangements utilizing the fundamental concepts of the present invention.

DETAILED DESCRIPTION OF EMBODIMENTS

The present invention relates generally to a composite material comprising a silica monolith nested in sponge, referred to herein as SiMNS. Any term or expression not expressly defined herein shall have its commonly accepted definition understood by a person skilled in the art.

In purification or extraction technology, a "monolith" is a continuous stationary-phase element cast as a column or other morphology in a single piece, as opposed to a packed column of porous particles. A monolith is characterized by a highly interconnected network of channels through the monolith. The adsorptive surface of the monolith is directly accessible to solutes as they pass through the network of channels through the monolith.

As used herein, a "sponge" means a porous mass of interlacing fibers, which may comprise any suitable material, such as a pure organic polymer.

In some embodiments, SiMNS is prepared through absorption of a hydrolyzed mixture of siloxanes into a sponge, and in situ gel formation within the sponge pores. Scanning electron microscopy (SEM) images show that monolithic silica layer forms over and/or around the sponge skeletons, such that they are mutually nested in the SiMNS. This nested composite structure of SiMNS enhances the mechanical flexibility of the material, allowing for reproducible production of desirable sizes and shapes of SPE cartridges without the need of using flits.

In some embodiments, the SiMNS may be functionalized to provide appropriate SPE options for selective and efficient extraction of specific contaminants. Functionalization may be accomplished by chemical or enzymatic modification of the silica surface area, or by admixing an absorbent or the like into the monolith such that it is exposed. For example, SPE cartridges packed with functionalized SiMNS-SO₃Na may have high extraction capacities, good stability in the pH range of 2 to 11. In a specific example, these materials can provide efficient enrichment of dipeptides in water. In another example, a carrier molecule such as a cyclodextrin may be added during or before polymerization, to be incorporated into the silica monolith.

Figure 1:
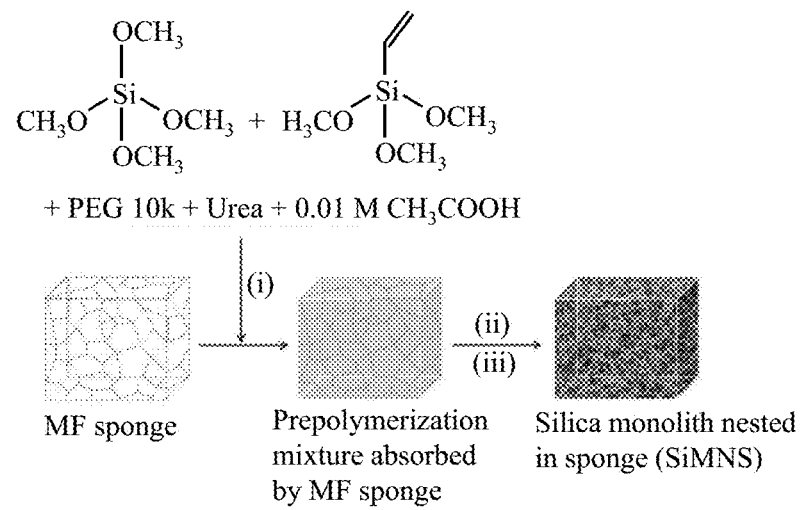
FIG. 1A shows a schematic representation of one embodiment of a scheme to prepare material comprising silica monolith nested in sponge (SiMNS).

FIG. 1 shows exemplary procedures for the preparation of SiMNS. In a first step, the siloxanes such as tetramethoxysilane (TMOS) and vinyltrimethoxysilane (VTMS) are hydrolyzed and then absorbed by a polymer sponge, such as a melamine formaldehyde (MF) sponge. Gel formation occurs within the sponge pores. The formed silica-sponge material may then be heated, for example, it may be incubated at 55° C. for 12 h and followed by 80° C. for 8 h. The synthesis process is simple and suitable for the preparation of large-size monoliths.

An alternative to TMOS is tetraethyl orthosilicate (TEOS). Alternatives to VTMS are methyltrimethoyxsilane (MTMS), glycidoxypropyltrimethoxysilane (GPTMS), 3-(trimethoxysilyl)propyl methacrylate (γ-MAPS), 3-mercaptopropyltrimethoxysilane (MPTMS), and 3-chloropropyltrimethoxysilane (CPTMS). These alternative reagents can be used to synthesis SiMNS according to the method described herein.

The sponge may comprise any suitable polymer, such as melamine formaldehyde resin or polyurethane.

Figure 2:
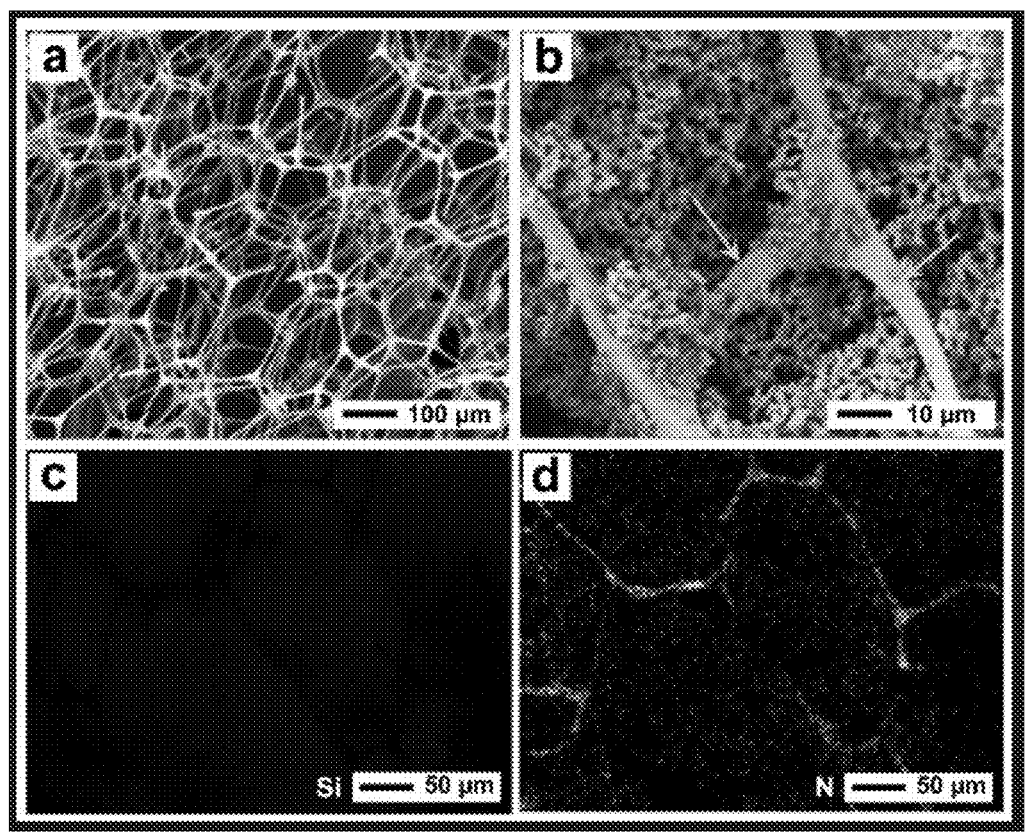
FIG. 2 shows scanning electron microscope images of (a) the MF sponge, (b) SiMNS; (c) EDX mapping image of silicon; and (d) EDX mapping image of nitrogen. The sponge skeleton in SiMNS is labelled with arrows in panel (b).

The resulting SiMNS features may be characterized by examining the morphological characteristics of the sponge and SiMNS using a scanning electron microscope (SEM). In the sponge, the macropore size may range from 100 to 200 μm and the skeleton size was ~5 μm (FIG. 2a).

Figure 3:
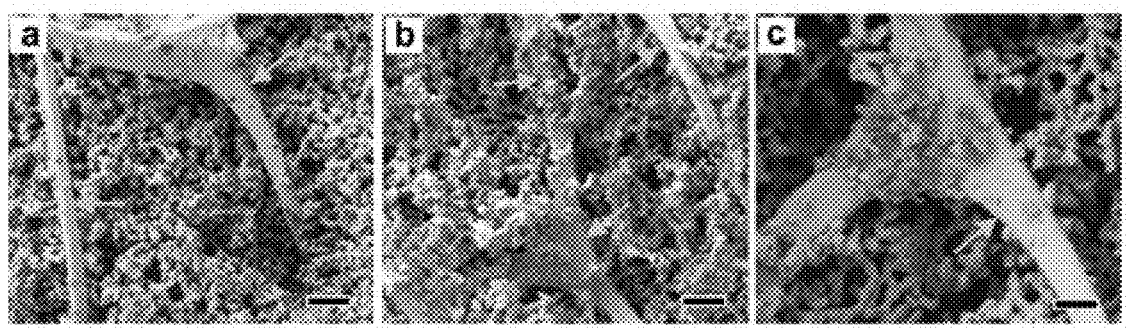
FIG. 3 shows SEM images at different magnifications. Sponge skeleton is labelled with arrows.
Figure 4:
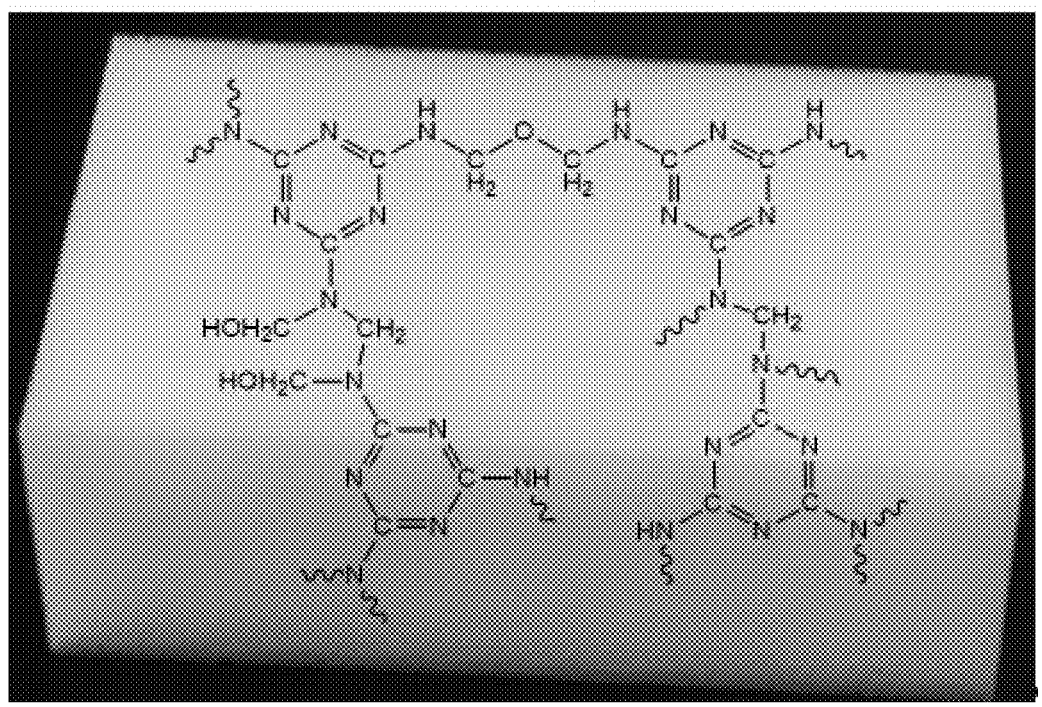
FIG. 4 shows chemical structure of one embodiment of a sponge.

The high size ratio of the macropore to the skeleton generated high porosity and offered space to inlay a monolithic silica matrix. FIG. 2b clearly shows the uniform silica monolith throughout the three-dimensional pores of the sponge. The sponge skeleton (marked by arrows in FIG. 2b, FIG. 3) is embedded through the whole silica monolith. This composite structure was also confirmed using energy dispersive X-ray spectroscopy mapping images shown in FIGS. 2c (silicon) and 2d (nitrogen). The silicon signal was derived from a silica monolith, while the nitrogen distribution was derived from the sponge skeleton (FIG. 4).

Thus, silica and the sponge skeletons were mutually nested, with an analogous structure to reinforced concrete. To some extent, the flexible sponge provides flexibility to prevent the SiMNS from cracking.

Figure 5:
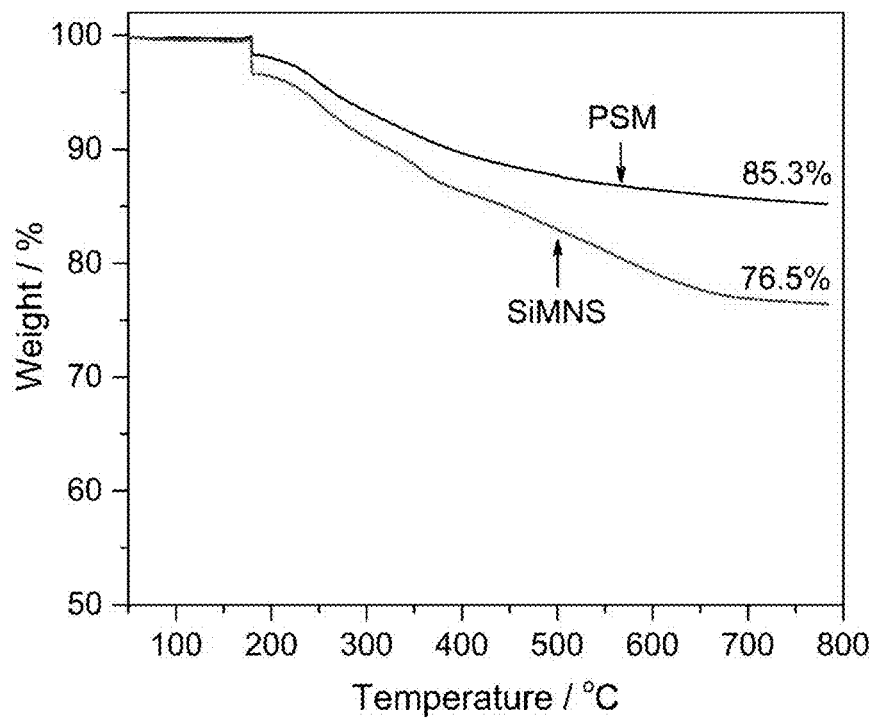
FIG. 5 shows thermogravimetric analysis (TGA) curves for a pure silica monolith (PSM) and a silica monolith nested in sponge (SiMNS).

TGA may be used to determine the mass fraction of the sponge in SiMNS. It was assumed that the residual should only be inorganic silica oxide. As shown in FIG. 5, a weight loss of 15% occurred for the PSM, arising from vinyl groups in the starting monomer VTMS. The percentage of the organic moiety in SiMNS was increased to 23% after incorporation of the sponge. Therefore, the sponge accounted for about 9.4% of the total weight of SiMNS.

Sponge Fraction in SiMNS.

a and b may be used to represent fractions of the inorganics in the pure silica monolith and SiMNS, respectively. The fraction of MF sponge in SiMNS was indicated by c, while the total weight of SiMNS used for the TGA measurement was m. Finally, b can be calculated by the following Equation (1), which was then converted into Equation (2).

$$b = \frac{m \times (1-c) \times a}{m} \quad (1)$$

$$c = 1 - \frac{b}{a} \quad (2)$$

According to TGA curves in FIG. 5, a=85% and b=77%, and so the sponge fraction, c, was determined to be 9.4%.

In other words, SiMNS is mainly composed of the silica monolith, which may allow it to maintain a rigid structure while providing enhanced mechanical flexibility.

Figure 6:
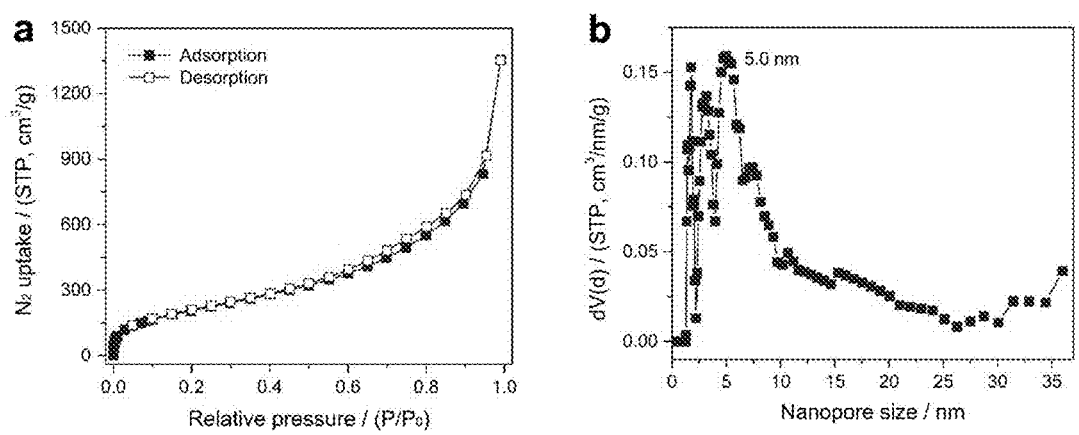
FIG. 6 shows (a) nitrogen adsorption-desorption isotherm, and (b) nanopore size of PSM.

The porosity of SiMNS after incorporation of the sponge may be measured using a mercury intrusion porosimeter (MIP) and nitrogen adsorption-desorption measurements. As shown in FIG. 2a, the macropore diameter for SiMNS ranged from 1 to 5 μm, which is larger than the macropore diameter for the PSM (1-2 μm). Silica monoliths usually demonstrate a hierarchically porous structure, and the nanopores in the skeleton contributed to a total surface area of 774 m²/g for the PSM (FIG. 6). In comparison, the surface area for SiMNS declined to 570 m²/g (FIG. 2b). This decrease in surface area is attributed to the incorporation of the sponge, as there are no nanopores present in the sponge.

According to FIG. 2c, the nanopore size for SiMNS was 4.8 nm, similar to that of the PSM (FIG. 6).

Figure 7:
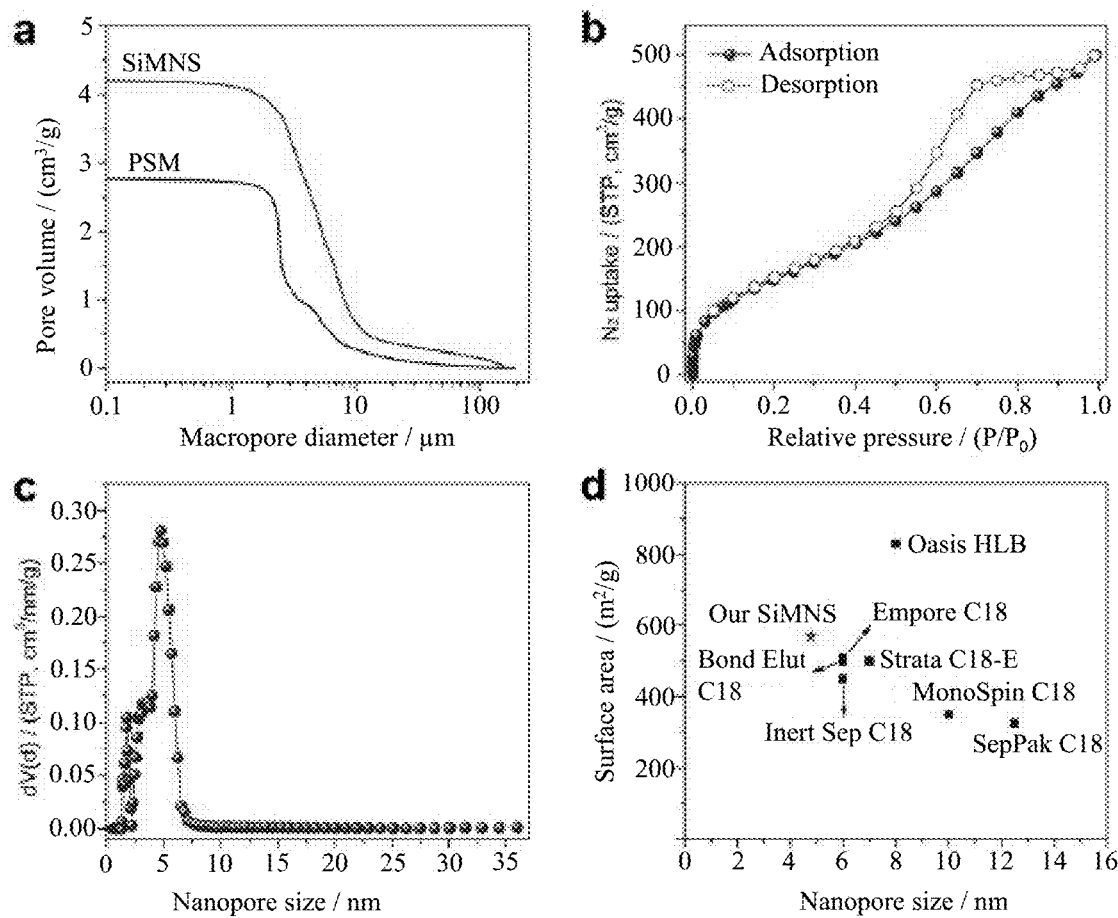
FIG. 7 (a) shows micropore diameter of PSM and SiMNS, (b) nitrogen adsorption-desorption isotherm of SiMNS, (c) nanopore size of SiMNS, and (d) porosity comparisons between SiMNS and particle sorbents packed in commercially available SPE cartridges.

The porosity of SiMNS compares favourably with that of the particle sorbents packed in several commercial SPE cartridges (FIG. 7d). SiMNS has a higher surface area than most of the particle sorbents, and the nanopore size in SiMNS is close to that of Bond Elut C18, Inert Sep C18, and Empore C18 sorbents.

Figure 8:
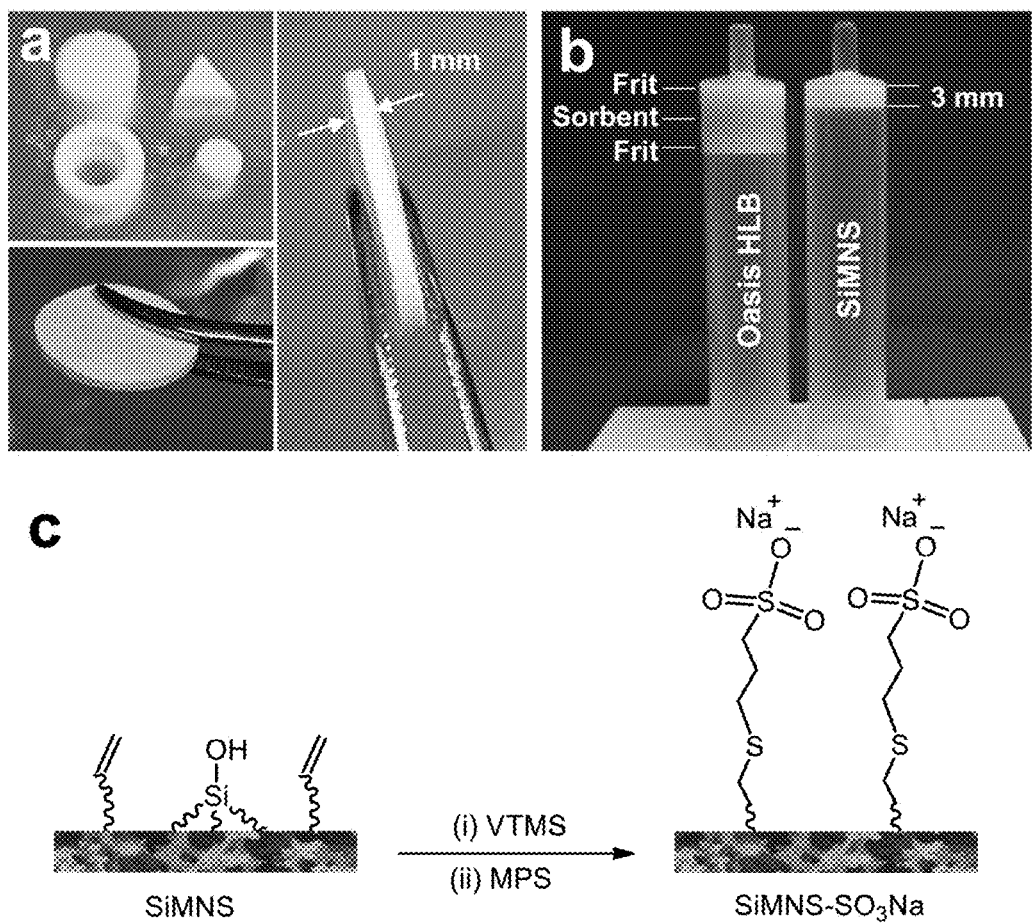
FIG. 8(a) shows photos of SiMNS of different shapes, (b) commercial Oasis HLB compared to SiMNS packed cartridges, (c) a schematic representation of the preparation of SiMNS-SO$_3$Na (treated with VTMS to improve vinyl group density and reacted with MPS via a thiol-ene click reaction).

SiMNS SPE Cartridges. A large-size bulk SiMNS can be cut into desired shapes and sizes, such as solid or hollow cylinders and films (FIG. 8a) because of the excellent mechanical flexibility. A SiMNS membrane at thickness of 1 mm maintains its high mechanical stability. For a perfect fit of SiMNS inside a syringe cartridge commonly used in SPE, a SiMNS membrane may be made with an appropriate diameter (e.g. 13.0 mm) and thickness (e.g. 3.0 mm) using a hole punch. Compared to particle-packed cartridges, such as Oasis HLB, the SiMNS-packed cartridge does not require frits (FIG. 8b). Accordingly, embodiments of this invention may allow the convenient production of a large number of SiMNS SPE cartridges.

Figure 9:
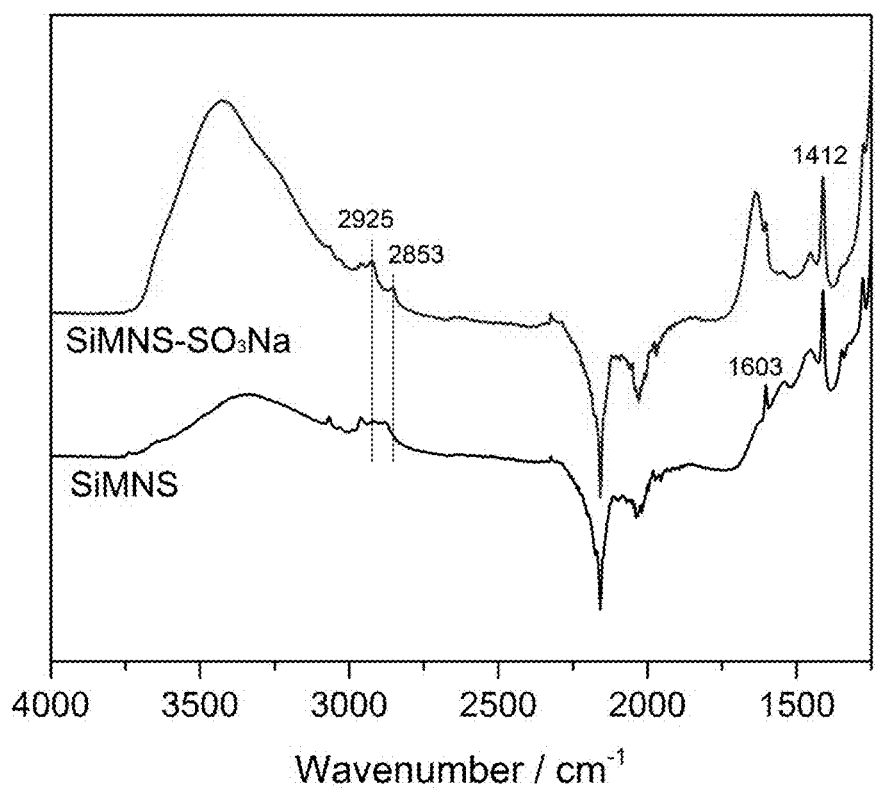
FIG. 9 shows FT-IR spectra of pristine SiMNS and SiMNS-SO$_3$Na.

The surface properties of SiMNS may be tuned or functionalized for specific applications. For example, SiMNS may be functionalized with a short chain sulfonic group for extraction of small peptides in water, because of the interactions between free amine groups of peptides and sulfonate groups. Small hydrophilic peptides are poorly removed during water treatment processes and can serve as precursors of disinfection by-products (DBPs) of toxicological relevance. Low extraction efficiencies for such peptides are achieved using commercial cartridges, impeding the detection and identification of these DBP precursors in water samples. SiMNS may be functionalized with 3-mercapto-1-propanesulfonic acid sodium salt (MPS) via the thiol-ene click reaction (SiMNS-$SO_3$Na, FIG. 8c). The surface modification was confirmed by FT-IR (FIG. 9).

For pristine SiMNS, the peak at 1412 $cm^{-1}$ was ascribed to the in-plane bending vibration of C—H (=$CH_2$), while the peak at 1603 $cm^{-1}$ represented the stretching vibration of C=C bond in vinyl groups. For SiMNS-$SO_3$Na, new absorption bands at 2853 and 2925 $cm^{-1}$ corresponded to C—H (—$CH_2$—) stretching vibrations, derived from the MPS moiety.

After developing SiMNS-$SO_3$Na SPE cartridges, their repeatability from cartridge to cartridge and from batch to batch was confirmed using the relative standard deviation (RSD) of Phe-Gly recoveries. The RSD values of recoveries obtained from cartridge-to-cartridge (n=8) and batch-to-batch (n=5) are 2% and 3%, respectively, demonstrating reproducible production of the SiMNS SPE cartridges.

Figure 10:
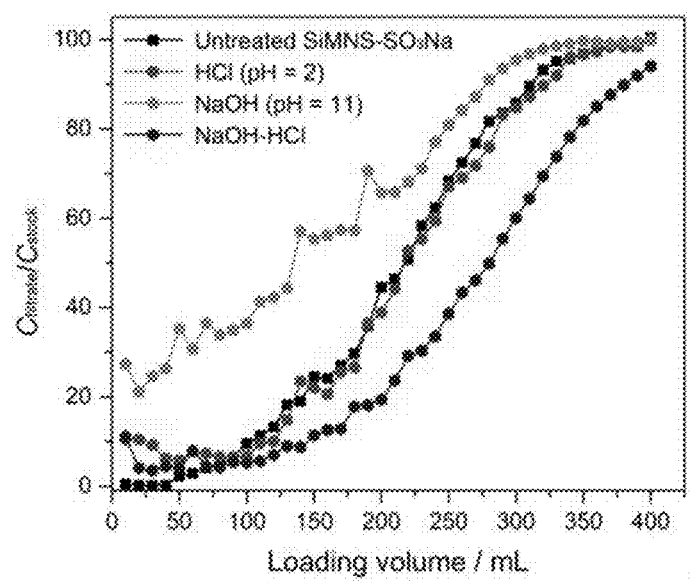
FIG. 10 shows breakthrough curves for the adsorption of Tyr-Val solution (28 mg/L) using an untreated SiMNS-SO$_3$Na cartridge and three cartridges treated with 10 mL aqueous solutions of HCl (pH 2), NaOH (pH 11), and NaOH followed by HCl, respectively.
Figure 11:
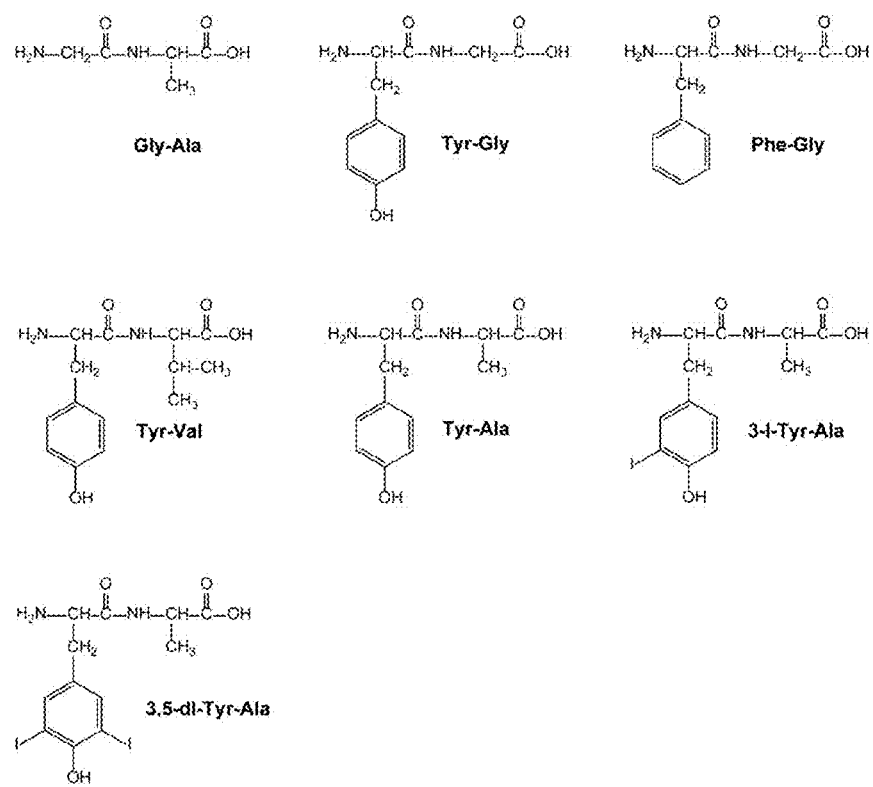
FIG. 11 shows chemical structures of dipeptides used to evaluate SPE cartridges.

The adsorption capacity of SiMNS-$SO_3$Na SPE cartridges was confirmed using Tyr-Val (28 mg/L) as a probe and obtained its adsorption breakthrough curves, shown in FIG. 10. The adsorption capacity for untreated SiMNS-$SO_3$Na SPE cartridge was 27 mg/g, determined at 10% of $C_{filtrate}/C_{stock}$ in breakthrough curve. The maximum adsorption capacity was 57 mg/g at 100% of $C_{filtrate}/C_{stock}$.

The HCl-treated SiMNS-$SO_3$Na SPE cartridge exhibited similar breakthrough volume and adsorption capacity to those of an untreated cartridge. The NaOH-treated cartridge had poor loading capability, because under strong basic condition SiMNS-$SO_3$Na remains instead of transforming to SiMNS-$SO_3$H for interacting with Tyr-Val. After washing with water and HCl (pH=2) solution, the adsorption capability of the NaOH—HCl-treated cartridge were regenerated. These results demonstrate that SiMNS-$SO_3$Na SPE cartridges are stable at pH 2 to 11. For enrichment of peptides, acidic solution precondition is preferred for achieving optimum extraction of the analytes.

Environmental Application of SiMNS SPE Cartridges.

Figure 12:
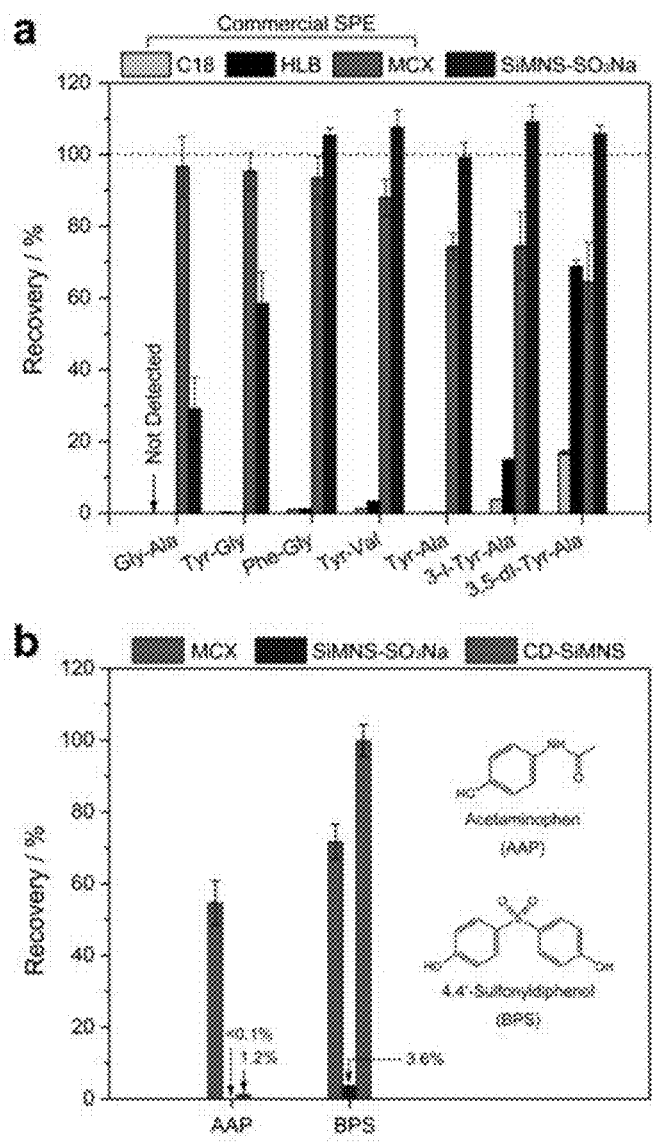
FIG. 12 shows (a) recovery of dipeptides of Sep-Pak C18, Oasis HLB, Oasis MCX, and SiMNS-SO$_3$Na SPE cartridges, (b0 recovery of phenols on Oasis MCX, SiMNS- SO₃Na and CD-SiMNS cartridges. Error bars indicate standard deviation of the mean of triplicate extractions.

SiMNS-$SO_3$Na SPE cartridges may be used in analysis of small peptides (di-, tri-, tetra- or penta-), as shown in FIG. 12a. Extraction of six dipeptides from water using these new SiMNS-$SO_3$Na SPE cartridges, followed by HPLC-MS/MS analysis, results in improved method detection limits (MDLs) of 0.02-1.3 ng/L and method quantification limits (MDLs) of 0.05-4.3 ng/L. Successful identification and quantification of three dipeptides, Tyr-Gly, Phe-Gly, and Tyr-Ala, from raw water demonstrate a useful application of SiMNS materials for environmental analysis of trace contaminants.

A range of functionalized SiMNS materials can be produced and tailored for various environmental and exposomic analyses. Other functional monomers for chemical modification via thiol-ene click reaction may also be used, e.g. I-octadecanethiol, cysteine, or glutathione.

In other embodiments, the SiMNS may be modified by (1) organosilicon reagents (e.g., n-octyltrimethoxysilane, and octadecyltrimethoxysilane) via condensation reaction between reagents and silicon hydroxyl groups on SiMNS surface; (2) by acrylates or methacrylates (e.g., 3-sulfopropyl methacrylate potassium salt), or vinyl-containing monomers (e.g., vinylphosphonic acid) via free radical polymerization reaction.

These new cartridges can provide highly efficient extractions of dipeptides and halogenated dipeptides with recoveries of 100% for 5 of the 7 peptides and 59% for Tyr-Gly and 29% for Gly-Ala. The reproducibility of these cartridges is excellent, demonstrated by the small error bars (2-9%, n=3). In comparison, commercial C18 and Oasis HLB cartridges showed recoveries lower than 5% for most dipeptides (FIG. 12a). The performance of the new SiMNS-$SO_3$Na was comparable with the MCX cartridges, which provided recoveries ranging from 64-97% for the peptides tested.

The selectivity of the SiMNS-$SO_3$Na for extraction of small peptides was examined, and compared the recoveries with those obtained using the MCX cartridge. Because most of the test peptides contained tyrosine (Tyr) and phenylalanine (Phe), AAP and BPS were chosen as interfering compounds. FIG. 12b shows that SiMNS-$SO_3$Na did not suffer interference from AAP and BPS, as the recoveries of the interfering compounds were as low as 0.03% and 3.6%. In contrast, AAP and BPS are well retained on MCX cartridges with recoveries of 55% for AAP and 72% for BPS, demonstrating possible interference in analysis of the small peptides. The difference in selectivity of SiMNS-$SO_3$Na from MCX is due to their surface chemistry. The benzene rings and pyrrolidone moieties in MCX polymeric surface provide π-π and hydrogen bonding interactions with phenols.

For the SiMNS-$SO_3$Na, short chain sulfonate groups effectively avoid retentions of these interfering compounds. These results demonstrate that SiMNS-$SO_3$Na has high selectivity for the small dipeptides. This high selectivity is needed to selectively concentrate the peptides at low levels in real water samples.

Figure 13:
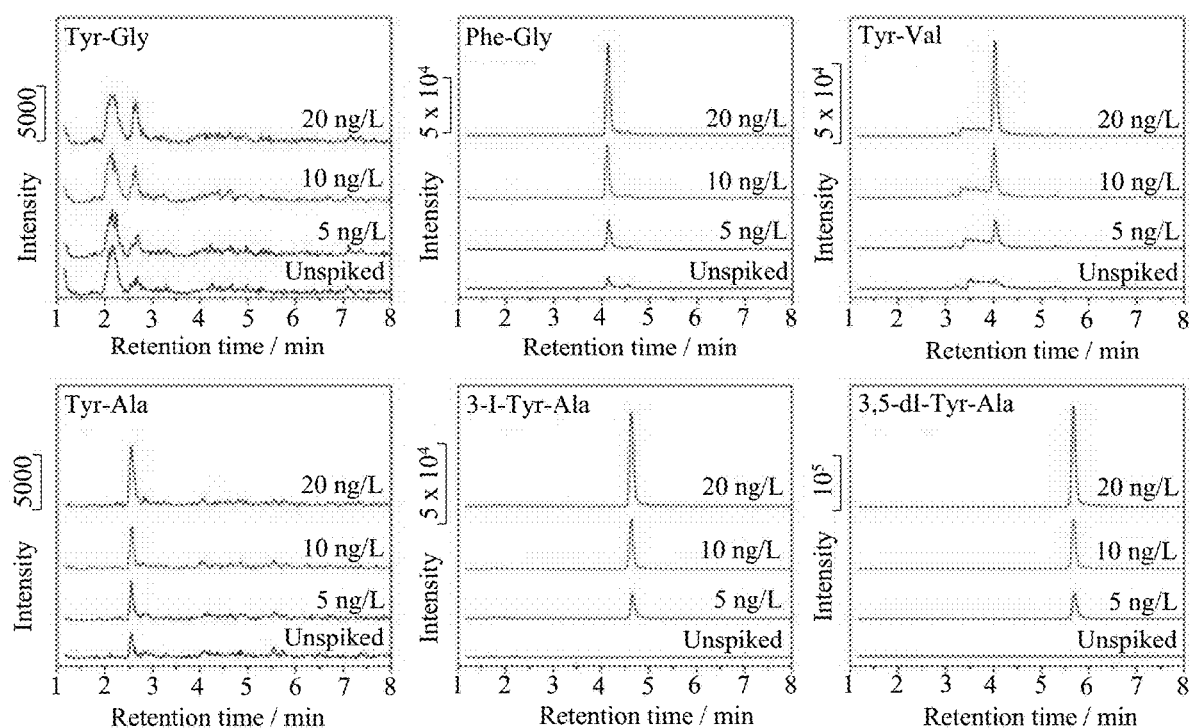
FIG. 13 shows selected ion chromatograms of dipeptides in unspiked and spiked raw water after extraction using SiMNS-SO₃Na cartridges. The 5-20 ng/L are the concentrations of dipeptides spiked in the raw water samples.

To demonstrate the application of the SiMNS-$SO_3$Na SPEs for trace analysis, additional extractions of raw water samples spiked with 1-20 ng/L each for Tyr-Gly, Phe-Gly, Tyr-Val, 3-I-Tyr-Ala, and 3,5-dI-Tyr-Ala, and 5-20 ng/L for Tyr-Ala were performed. The extracts were analyzed using HPLC-MS/MS, as shown in FIG. 13.

As summarized in Table S3, the relationship of peak areas vs. concentrations tested is linear.

TABLE S3

Calibration curve parameters of the SiMNS-
SO₃Na SPE-HPLC-MS/MS method for analysis of
raw water samples spiked with dipeptides

| Dipeptides | Calibration curve | $R^2$ | Calibration curve linearity range (ng/L) |
|---|---|---|---|
| Tyr-Gly | y = 1168 x + 6787 | 0.984 | 1-20 |
| Phe-Gly | y = 26752 x + 33046 | 0.990 | 1-20 |
| Tyr-Val | y = 21056 x + 22371 | 0.998 | 1-20 |
| Tyr-Ala | y = 1682 x + 12350 | 0.934 | 5-20 |
| 3-I-Tyr-Ala | y = 19140 x + 5366 | 0.993 | 1-20 |
| 3,5-dI-Tyr-Ala | y = 90060 x + 31021 | 0.998 | 1-20 | y = a x + b, where the x is spiked dipeptide concentration in raw water, and the y is peak area after 450-fold preconcentration.

Table 2 shows that the MDLs are 0.02-1.3 ng/L, and MQLs range from 0.05-4.3 ng/L. Additionally, Tyr-Gly, Phe-Gly and Tyr-Ala were detected in unspiked raw water (FIG. 6) and determined to be 1.2±0.5 ng/L for Phe-Gly, 7±3 ng/L for Tyr-Ala and estimated 6±0.8 ng/L for Tyr-Gly from triplicate extractions and HPLC-MS/MS analysis.

TABLE 2

Performance of the SiMNS-SO₃Na SPE-HPLC-
MS/MS method for the 6 dipeptides

| Dipeptides | Retention time (min) | LOD[a] (μg/L) | LOQ[a] (μg/L) | MDL[b] (ng/L) | MQL[b] (ng/L) | Unspiked raw water[c] (ng/L) |
|---|---|---|---|---|---|---|
| Tyr-Gly | 2.6 | 0.05 | 0.09 | 1.3 | 4.3 | 6 ± 0.8 |
| Phe-Gly | 4.1 | 0.04 | 0.06 | 0.07 | 0.2 | 1.2 ± 0.5 |
| Tyr-Val | 4.0 | 0.02 | 0.03 | 0.4 | 1.1 | n.d. |
| Tyr-Ala | 2.5 | 0.05 | 0.09 | 1.3 | 4.3 | 7 ± 3 |
| 3-I-Tyr-Ala | 4.6 | 0.03 | 0.06 | 0.07 | 0.3 | n.d. |
| 3,5-dI-Tyr-Ala | 5.7 | 0.01 | 0.02 | 0.02 | 0.05 | n.d. |

[a]Limits of detection (LOD) and limits of quantification (LOQ) were calculated for HPLC-MS/MS method (without SPE). The average blank ($S_{blank}$) and the standard deviation ($\sigma_{blank}$) of peak areas were calculated through triplicate analysis of optima water (blank). The LOD was determined as the concentration of the standard that gives peak area equal to ($S_{blank}$ + $3\sigma_{blank}$). The LOQ was determined as the concentration of the standard that gives peak area equal to ($S_{blank}$ + $10\sigma_{blank}$).
[b]MDL and MQL were obtained from SiMNS-SO₃Na SPE-HPLC-MS/MS analysis of raw water samples containing 1, 3, 5, 10, 20 ng/L of each dipeptide. The MDL and MQL were calculated as three and ten times the standard deviation of the method blank signal divided by the slope, respectively.
[c]The concentrations of detected dipeptides in unspiked raw water samples were calculated as the intercept divided by the slope (Table S3), and standard deviations were determined through propagation of uncertainty.
'n.d.': 'not detected'.

In another example, SiMNS may be functionalized with a surface-borne carrier molecule such as a cyclodextrin or cyclodextrin derivative, an acrylate or methacrylate (e.g., 3-sulfopropyl methacrylate potassium salt), or a vinyl-containing monomer (e.g., vinylphosphonic acid). The carrier may be admixed into the prepolymerization mixture.

Figure 14:
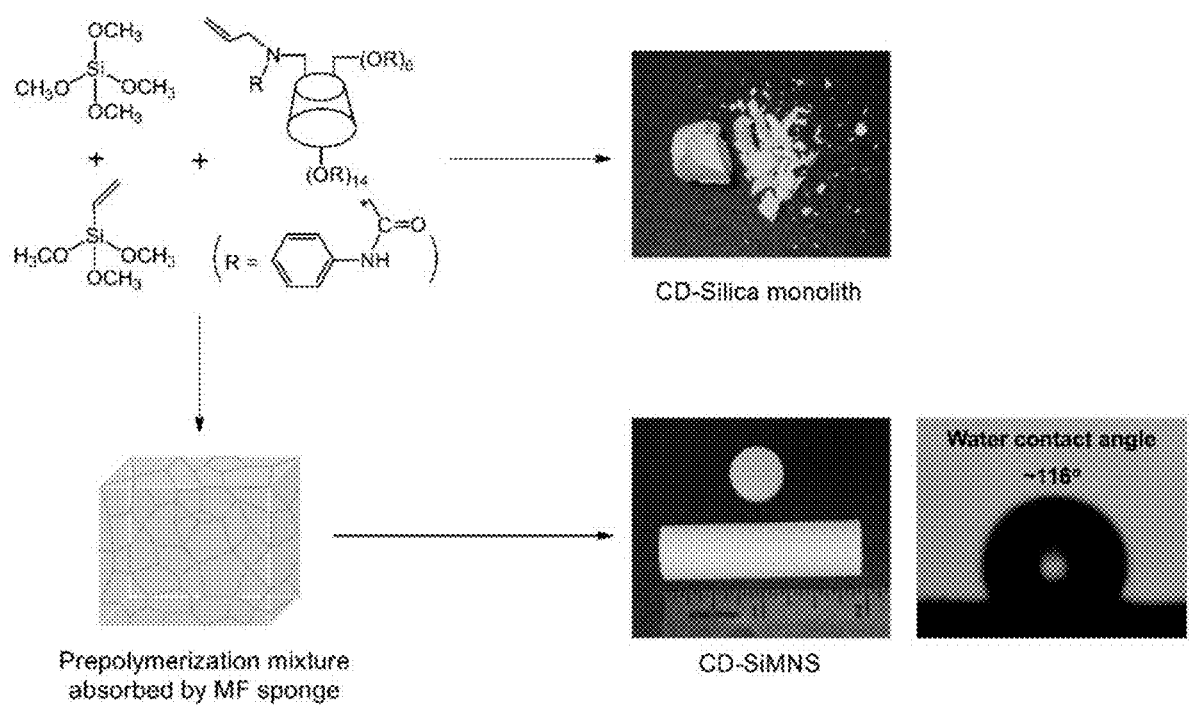
FIG. 14 shows a schematic of the preparation of CD-SiMNS.
Figure 15:
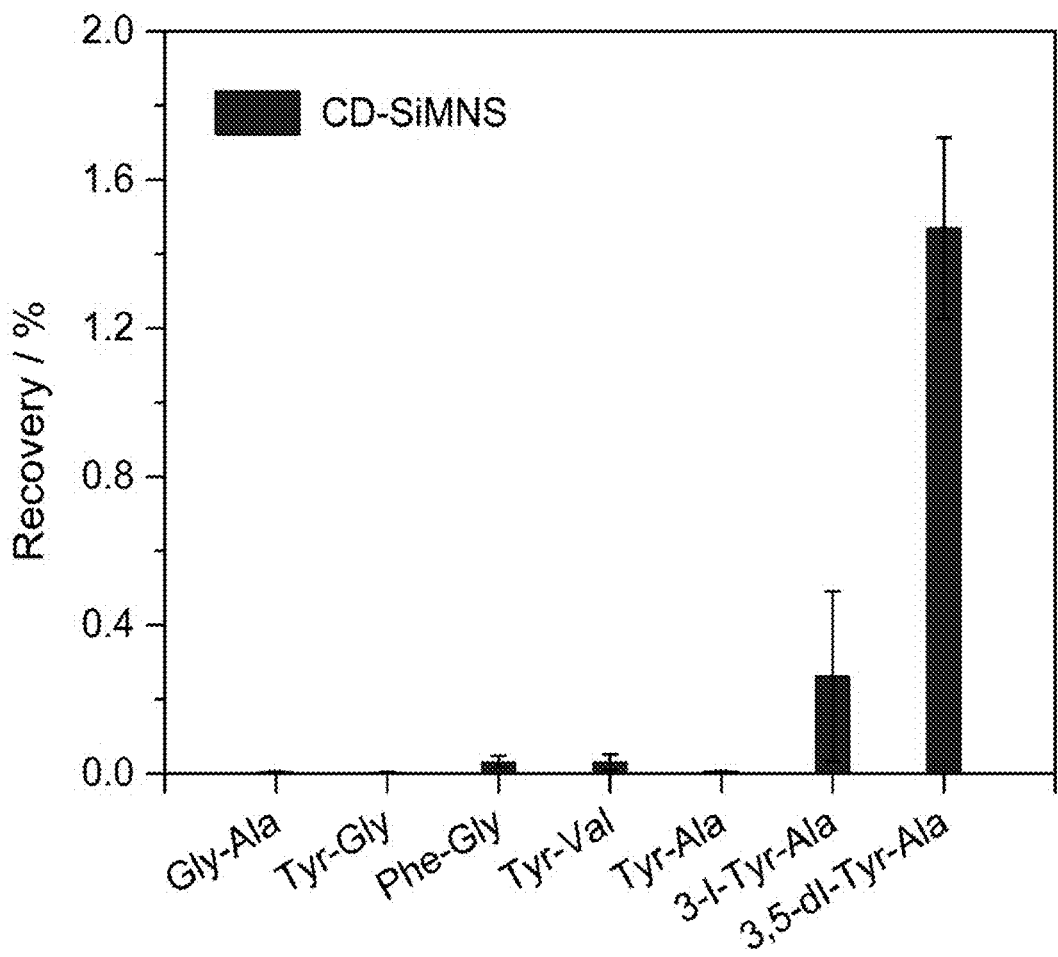
FIG. 15 shows a graph of dipeptide recovery on CD-SiMNS cartridge.

In one embodiment, to selectively extract 4,4'-sulfonyldiphenol (bisphenol S or BPS), the prepolymerization mixture may comprise siloxanes (e.g. VTMS, TMOS) and a β-cyclodextrin (CD) derivative, to produce a composite monolith denoted as CD-SiMNS (FIG. 14). CD-SiMNS has good cuttability. The composition of the prepolymerization mixture and detailed reaction conditions may be found in Zhang et al. Anal. Chem. 2011, 83, 3616-3622 (the entire contents of which are incorporated herein by reference, for all purposes).

The CD-SiMNS cartridges were able to extract BPS with substantially 100% recovery, without extracting AAP and dipeptides (FIG. 5b, FIG. 12b).

EXAMPLES

The following examples are provided to illustrate embodiments of the invention and are not intended to limit the claimed invention in any way.

Chemicals and Materials.

Tetramethoxysilane (TMOS), vinyltrimethoxysilane (VTMS), urea, polyethylene glycol (PEG, Mn=10 000), 3-mercapto-1-propanesulfonic acid sodium salt (MPS), α,α'-azoisobutyronitrile (AIBN), triethylamine (TEA), formic acid (FA), Tyr-Gly, Tyr-Ala, Gly-Ala, Phe-Gly, Tyr-Val, acetaminophen (AAP) and 4,4'-sulfonyldiphenol (BPS) were purchased from Sigma-Aldrich (St. Louis, MO). 3-Iodo-Tyr-Ala (3-I-Tyr-Ala) and 3,5-di-iodo-Tyr-Ala (3,5-dI-Tyr-Ala) were obtained from the Chinese Peptide Company (Hangzhou, China). Optima water, methanol, acetic acid, and acetonitrile (ACN) were purchased from Fisher Scientific (Fair Lawn, NJ). Sep-Pak C18 cartridges (3 mL, 200 mg sorbent), Oasis HLB cartridges (6 mL, 200 mg sorbent), and MCX cartridges (6 mL, 150 mg sorbent) were obtained from Waters (Milford, MA). Empty syringe cartridges (6 mL) were purchased from Agilent Technologies (Santa Clara, CA). MF sponges (RioRand) were purchased from Amazon.

Preparation of SiMNS.

FIG. 1 shows the three steps to prepare SiMNS. At Step i, solutions of TMOS (10.8 mL) and VTMS (3.6 mL), and solids of PEG (3.0 g) and urea (2.7 g) were added to an aqueous solution of acetic acid (0.01 M, 30 mL). The mixture was stirred in an ice-water bath for 1 h, and then absorbed by the sponge. At Step ii, the saturated sponge was maintained in the incubator at 55° C. for 12 h, and at Step iii, increased to 80° C. for 8 h. The resulting composite silica monolith nested in sponge (SiMNS) was washed with water, and cut into cylindrical membranes with a diameter of 15 mm and thickness of ~10 mm. As a control, a pure silica monolith (PSM) was prepared using the same steps (i-iii) without incorporation of the sponge.

Surface Functionalization of SiMNS.

Eight SiMNS membranes were placed into a 50-mL flask with methanol (20 mL), VTMS (3.8 mL), and TEA (1.75 mL). After reaction under reflux for 12 h, SiMNS membranes were washed with methanol (30 mL×3) three times. Then, a solution of MPS (1.0 g) in methanol/water (24 mL, 3/1, v/v) and AIBN (0.1 g) were added. Thiol-ene click reaction of MPS with vinyl groups on SiMNS surface was carried out at 60° C. for 5 h. The sulfonate-functionalized monolith, denoted as SiMNS-SO₃Na, was obtained after washing with water (30 mL×5) five times.

Characterization.

The morphology study was carried out on a field emission scanning electron microscope (FESEM, Zeiss, Germany). For thermogravimetric analysis (TGA), samples were heated at 10° C./min in air using a Discovery TGA instrument (TA instruments, Waters). The macropore diameter of SiMNS was determined by a mercury intrusion porosimeter (MIP, Quantachrome Instruments, Boynton Beach, FL). Nitrogen adsorption-desorption measurements were performed on an Autosorb iQ (Quantachrome Instruments). Samples were outgassed under vacuum at 100° C. for 4 h before measurement. The surface area was calculated using the Brunauer-Emmett-Teller (BET) method. Nanopore size was determined by the NLDFT approach. FT-IR spectra were collected on a Nicolet iS50 FT-IR spectrometer with the attenuated total reflection mode (Thermo Fisher Scientific, Waltham, MA).

SPE Method.

The SiMNS-SO$_3$Na membranes (13-mm diameter and 3-mm thickness) were packed into empty syringe cartridges. The SPE process was done on a Supelco vacuum manifold. Briefly, SiMNS-SO$_3$Na SPE cartridges were equilibrated with methanol (2 mL), acidic water with FA (4 mL, 0.25%, v/v) and water (4 mL), successively. Standard water samples containing seven dipeptides (450 mL, each at 6 g/L) were passed through cartridges at a flow rate of ~2-3 mL/min. After washing with optima water (2 mL), dipeptides were eluted with ammonium hydroxide solution (5 wt. % in methanol, 10 mL). The eluent was concentrated to 100 µL under a gentle nitrogen stream (20-50 KPa) for ~2.5 h, then reconstituted with optima water to 2 mL. The dipeptide concentrations in standard water samples and eluent were determined by HPLC-MS/MS (MRM) method described in the following section. The recovery was calculated by the following equation:

$$\text{Recovery} = \frac{C_{eluent} V_{eluent}}{C_0 V_0} \times 100\%$$

where $C_0$ (µg/L) and $C_{eluent}$ (µg/L) are dipeptide concentrations in water samples and eluent, respectively, and $V_0$ (L) and $V_{eluent}$ (L) are the corresponding volumes.

Based on the breakthrough curves (FIG. 4), the breakthrough volumes and the adsorption capacities at 10% of $C_{filtrate}/C_{stock}$ were determined, as well as the maximum adsorption capacities at 100% of $C_{filtrate}/C_{stock}$.

Application for Analysis of Raw Water.

Raw water samples of North Saskatchewan River were collected. The water samples were filtered using 1.5 µm glass microfiber filters (Whatman), followed by 0.45 µm nylon membrane disk filters, and then stored at 4° C. before analysis. The filtrations were necessary to remove particles to avoid blockage of the SPE during extraction. To evaluate SiMNS-SO$_3$Na SPE cartridges for extraction of analytes at trace levels, dipeptides were spiked at five different concentration levels (1, 3, 5, 10 and 20 ng/L) into the filtered raw water samples (450 mL, with 0.25% FA, v/v). Additionally, triplicate unspiked raw water samples were analyzed as the authentic samples. After SPE, the eluent was reconstituted to a final volume of 1 mL, and analyzed using the HPLC-MS/MS (MRM) method as follows.

HPLC-MS/MS (MRM) Method.

HPLC separations were performed on an Agilent 1290 series LC system equipped with a binary pump, an autosampler with temperature control, and a Luna C18(2) column (100×2.0 mm i.d., 3-µm particles; Phenomenex, Torrance, CA). The autosampler was kept at 4° C., and the injection volume of each sample was 20 µL. Mobile phase A and B

TABLE S1

Detailed SPE conditions.

| Cartridges | C18, HLB[a] | MCX, SiMNS-SO$_3$Na | CD-SiMNS |
|---|---|---|---|
| Condition (2 mL) | Methanol | Methanol | Methanol |
| Equilibrate (4 mL) | H$_2$O (0.25% FA)[b] | H$_2$O (0.25% FA) and H$_2$O | H$_2$O |
| Load sample | 450 mL (0.25% FA, dipeptides, each at 6 µg/L) | 450 mL (dipeptides or phenols, each at 6 µg/L) | 450 mL (dipeptides or phenols, each at 6 µg/L) |
| Wash (2 mL) | H$_2$O (0.25% FA) | H$_2$O | H$_2$O |
| Elute (10 mL) | Methanol (0.25% FA) | Methanol (5 wt. % NH$_3$·H$_2$O) | Methanol |

[a]According to our previously reported work (G. Huang, P. Jiang, L. K. Jmaiff Blackstock, D. Tian, and X.-F. Li, *Environ. Sci. Technol.*, 2018, 52, 4218-4226).
[b]0.25% formic acid (FA): v/v.

The adsorption capacity of SiMNS-SO$_3$Na SPE cartridge was evaluated using the breakthrough experiments. A stock solution of Tyr-Val ($C_{stock}$=28 mg/L) continuously flew through the cartridge after equilibration with water (4 mL). The filtrates were collected, each at 10 mL. The Tyr-Val concentrations ($C_{filtrate}$, mg/L) in filtrates were quantified using a UV-vis spectrophotometer at 223 nm. The breakthrough curve was obtained by plotting $C_{filtrate}/C_{stock}$ versus loading volume.

To test the stability of SiMNS-SO$_3$Na SPE cartridges, three cartridges were treated with 10 mL aqueous solutions of HCl (pH=2), NaOH (pH=11) and NaOH (pH=11) followed by HCl (pH=2), respectively. Breakthrough curves of these three treated cartridges were obtained using the same procedure described above. The adsorption capacities (mg/g, loading content of Tyr-Val per gram of SiMNS-SO$_3$Na membrane) were calculated by the following equation:

$$\text{Absorption capacity} = \frac{\Sigma(C_{stock} - C_{filtrate}) V_{filtrate}}{m}$$

where $V_{filtrate}$ (0.01 L) is the volume of each filtrate collected, and m (g) is the SiMNS-SO$_3$Na membrane weight.

were water (0.1% FA) and ACN (0.1% FA), respectively. The flow rate was set at 170 µL/min, with a gradient elution increasing mobile phase B from 5% to 70% in 15 min. A triple quadrupole ion-trap tandem mass spectrometer (SCIEX QTRAP 5500) was coupled with the HPLC to perform MS/MS (MRM) quantification of peptides. The MRM transition ions of the seven dipeptides, AAP and BPS are described in Table S1.

TABLE S1

MRM transition ions (Q1 and Q3 mass) and mass spectrometry parameters: declustering potential (DP), collision energy (CE), and collision cell exit potential (CXP).

| | Q1 (m/z) | Q3 (m/z) | DP (V) | CE (V) | CXP (V) |
|---|---|---|---|---|---|
| Gly-Ala | 146.9 | 90.0 | 49.1 | 13.8 | 11.3 |
| | | 43.9 | 54.3 | 26.4 | 7.1 |
| Tyr-Gly | 239.1 | 136.1 | 56.0 | 21.0 | 12.0 |
| | | 107.0 | 56.0 | 57.8 | 10.4 |
| Phe-Gly | 223.1 | 120.1 | 71.8 | 22.4 | 10.2 |
| | | 91.1 | 71.8 | 61.0 | 8.0 |
| Tyr-Val | 281.1 | 136.1 | 75.0 | 23.6 | 12.0 |
| | | 119.0 | 75.0 | 40.0 | 14.0 |
| Tyr-Ala | 253.2 | 135.7 | 75.0 | 24.0 | 18.0 |
| | | 119.1 | 75.0 | 36.0 | 18.0 |

TABLE S1-continued

MRM transition ions (Q1 and Q3 mass) and mass spectrometry parameters: declustering potential (DP), collision energy (CE), and collision cell exit potential (CXP).

| | Q1 (m/z) | Q3 (m/z) | DP (V) | CE (V) | CXP (V) |
|---|---|---|---|---|---|
| 3-I-Tyr-Ala | 379.0 | 262.0 | 77.4 | 25.4 | 7.7 |
| | | 135.0 | 79.1 | 44.3 | 12.0 |
| 3,5-dI-Tyr-Ala | 504.9 | 387.9 | 68.6 | 28.5 | 11.0 |
| | | 261.0 | 81.7 | 47.7 | 24.5 |
| AAP | 152.0 | 110.1 | 62.2 | 22.4 | 12.7 |
| | | 93.0 | 112.1 | 29.8 | 8.3 |
| BPS | 251.1 | 157.2 | 160.7 | 21.8 | 13.5 |
| | | 109.1 | 160.0 | 29.8 | 13.8 |

The MS parameters were optimized as follows: ion-spray voltage, 5500 V; source temperature, 500° C.; gas 1, 45 arbitrary units; gas 2, 40 arbitrary units; curtain gas, 30 arbitrary units; accumulation time for each ion pair, 50 ms. System control and data collection were done by Analyst software (version 1.5.2, AB SCIEX, Framingham, MA).

Interpretation

References in the specification to "one embodiment", "an embodiment", etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to affect or connect such module, aspect, feature, structure, or characteristic with other embodiments, whether or not explicitly described. In other words, any module, element or feature may be combined with any other element or feature in different embodiments, unless there is an obvious or inherent incompatibility, or it is specifically excluded.

It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation. The terms "preferably," "preferred," "prefer," "optionally," "may," and similar terms are used to indicate that an item, condition or step being referred to is an optional (not required) feature of the invention.

The singular forms "a," "an," and "the" include the plural reference unless the context clearly dictates otherwise. The term "and/or" means any one of the items, any combination of the items, or all of the items with which this term is associated. The phrase "one or more" is readily understood by one of skill in the art, particularly when read in context of its usage.

The term "about" can refer to a variation of 5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values and ranges proximate to the recited value or range that are equivalent in terms of the functionality of the composition, or the embodiment.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc.

As will also be understood by one skilled in the art, all language such as "between", "up to", "at least", "greater than", "less than", "more than", "or more", and the like, include the number(s) recited and such terms refer to ranges that can be subsequently broken down into sub-ranges as discussed above. In the same manner, all ratios recited herein also include all sub-ratios falling within the broader ratio.

REFERENCES

All publications, patents and patent applications mentioned in this specification are indicative of the level of skill of those skilled in the art to which this invention pertains and are herein incorporated by reference to the same extent as if each individual publication, patent, or patent applications was specifically and individually indicated to be incorporated by reference.

(1) Pichon, V., J. Chromatogr. A 2000, 885, 195-215.
(2) Plotka-Wasylka, J.; Szczepañska, N.; de la Guardia, M.; Namienik, J., TrAC Trends in Anal. Chem. 2015, 73, 19-38.
(3) Nema, T.; Chan, E. C. Y.; Ho, P. C., Talanta 2010, 82, 488-494.
(4) Huck, C. W.; Bonn, G. K., J. Chromatogr. A 2000, 885, 51-72.
(5) Namera, A.; Saito, T., TrAC Trends Anal. Chem. 2013, 45, 182-196.
(6) Nema, T.; Chan, E. C. Y.; Ho, P. C., J. Sep. Sci. 2011, 34, 1041-1046.
(7) Nakanishi, K.; Tanaka, N., Acec. Chem. Res. 2007, 40, 863-873.
(8) Guiochon, G., J. Chromatogr. A 2007, 1168, 101-168.
(9) Nuñez, O.; Nakanishi, K.; Tanaka, N., J. Chromatogr. A 2008, 1191, 231-252.
(10) Ou, J.; Liu, Z.; Wang, H.; Lin, H.; Dong, J.; Zou, H., Electrophoresis 2015, 36, 62-75.
(11) Tanaka, N.; McCalley, D. V., Anal. Chem. 2015, 88, 279-298.
(12) Svec, F.; Lv, Y., Anal. Chem. 2014, 87, 250-273.
Hara, T.; Futagami, S.; De Malsche, W.; Eeltink, S.; Terryn, H.; Baron, G. V.; Desmet, G., Anal. Chem. 2017, 89, 10948-10956.
Wu, C.; Liang, Y.; Yang, K.; Min, Y.; Liang, Z.; Zhang, L.; Zhang, Y., Anal. Chem. 2016, 88, 1521-1525.
(15) Horie, K.; Kamakura, T.; Ikegami, T.; Wakabayashi, M.; Kato, T.; Tanaka, N.; Ishihama, Y., Anal. Chem. 2014, 86, 3817-3824.
(16) Lin, H.; Ou, J.; Zhang, Z.; Dong, J.; Wu, M.; Zou, H., Anal. Chem. 2012, 84, 2721-2728.
(17) Dong, M.; Wu, M.; Wang, F.; Qin, H.; Han, G.; Dong, J.; Wu, R. a.; Ye, M.; Liu, Z.; Zou, H., Anal. Chem. 2010, 82, 2907-2915.
(18) Chen, M.; Zhang, J.; Zhang, Z.; Yuan, B.; Yu, Q.; Feng, Y., J. Chromatogr. A 2013, 1284, 118-125.
(19) Lin, Z.; Pang, J.; Yang, H.; Cai, Z.; Zhang, L.; Chen, G., Chem. Commun. 2011, 47, 9675-9677.

(20) Zhang, Z.; Wu, M.; Wu, R.; Dong, J.; Ou, J.; Zou, H., Anal. Chem. 2011, 83, 3616-3622.
(21) Ou, J.; Li, X.; Feng, S.; Dong, J.; Dong, X.; Kong, L.; Ye, M.; Zou, H., Anal. Chem. 2007, 79, 639-646.
(22) Liu, J.; Wang, F. J.; Lin, H.; Zhu, J.; Bian, Y. Y.; Cheng, K.; Zou, H. F., Anal. Chem. 2013, 85, 2847-2852.
(23) Miyazaki, S.; Morisato, K.; Ishizuka, N.; Minakuchi, H.; Shintani, Y.; Furuno, M.; Nakanishi, K., J. Chromatogr. A 2004, 1043, 19-25.
(24) Hayase, G.; Kanamori, K.; Abe, K.; Yano, H.; Maeno, A.; Kaji, H.; Nakanishi, K., ACS Appl. Mater. Interfaces 2014, 6, 9466-9471.
(25) Ruan, C.; Ai, K.; Li, X.; Lu, L., Angew. Chem. Int. Ed. 2014, 53, 5556-5560.
(26) Nguyen, D. D.; Tai, N.; Lee, S.; Kuo, W., Energy Environ. Sci. 2012, 5, 7908-7912.
(27) Pham, V. H.; Dickerson, J. H., ACS Appl. Mater. Interfaces 2014, 6, 14181-14188.
(28) Dotson, A.; Westerhoff, P., J. AWWA 2009, 101, 101-115.
(29) How, Z. T.; Linge, K. L.; Busetti, F.; Joll, C. A., Environ. Sci. Technol. 2017, 51, 4870-4876.
(30) Shah, A. D.; Mitch, W. A., Environ. Sci. Technol. 2012, 46, 119-131.
(31) Huang, G.; Jiang, P.; Li, X.-F., Anal. Chem. 2017, 89, 4204-4209.
(32) Huang, G.; Jiang, P.; Jmaiff Blackstock, L. K.; Tian, D.; Li, X.-F., Environ. Sci. Technol. 2018, 52, 4218-4226.

The invention claimed is:

1. A porous composite material comprising a silica monolith mutually nested in a melamine-formaldehyde (MF) sponge comprising a porous mass of interlacing fibers, such that the silica monolith is disposed within the porous mass, around the fibers.

2. The porous composite material of claim 1 further comprising surface sulfonic groups.

3. The porous composite material of claim 1 further comprising a surface cyclodextrin.

4. A method of extracting a bisphenol from a sample, comprising a step of passing the sample through a porous composite material as claimed in claim 3.

5. A method of extracting a peptide from a sample, comprising a step of passing the sample through a porous composite material as claimed in claim 2.

6. The method of claim 5 wherein the peptide is a dipeptide.

7. The porous composite material of claim 1 which further has a macropore diameter of between about 1 μm and about 5 μm.

8. The porous composite material of claim 7 which further has a nanopore size of about 4.8 nm.

9. The porous composite material of claim 1 which is further surface modified with an organosilicon reagent via a condensation reaction with silicon hydroxyl groups.

10. The porous composite material of claim 1 which is further surface modified with an acrylate or methacrylate.

11. The porous composite material of claim 1 which is further surface modified with a vinyl-containing monomer via a free radical polymerization reaction.

12. A solid phase extraction membrane comprising the porous composite material of claim 1.

13. The membrane of claim 12 further having a thickness of between about 1 mm and about 3 mm.

* * * * *